United States Patent
Marrone

(10) Patent No.: US 12,116,335 B2
(45) Date of Patent: Oct. 15, 2024

(54) PROCESS FOR PRODUCING FEED-GRADE UREA

(71) Applicant: Casale SA, Lugano (CH)

(72) Inventor: Leonardo Marrone, Mercallo (IT)

(73) Assignee: Casale SA, Lugano (CH)

(*) Notice: Subject to any disclaimer, the term of this patent is extended or adjusted under 35 U.S.C. 154(b) by 0 days.

(21) Appl. No.: 18/035,030

(22) PCT Filed: Sep. 10, 2021

(86) PCT No.: PCT/EP2021/074921
§ 371 (c)(1),
(2) Date: May 2, 2023

(87) PCT Pub. No.: WO2022/096183
PCT Pub. Date: May 12, 2022

(65) Prior Publication Data
US 2023/0303485 A1    Sep. 28, 2023

(30) Foreign Application Priority Data
Nov. 6, 2020 (EP) ............................ 20206206

(51) Int. Cl.
*C07C 273/16* (2006.01)
*C05C 9/00* (2006.01)

(52) U.S. Cl.
CPC ............ *C07C 273/16* (2013.01); *C05C 9/005* (2013.01)

(58) Field of Classification Search
None
See application file for complete search history.

(56) References Cited

U.S. PATENT DOCUMENTS

| | | | |
|---|---|---|---|
| 3,251,879 A * | 5/1966 | Rosenbloom | C05C 9/005 564/73 |
| 4,231,960 A * | 11/1980 | Schmidt | C07C 273/16 564/73 |
| 5,120,345 A * | 6/1992 | Kayaert | C05C 3/005 71/30 |
| 2019/0194127 A1* | 6/2019 | Mostert | B01J 4/008 |

FOREIGN PATENT DOCUMENTS

WO    2005/049193 A1    6/2005

OTHER PUBLICATIONS

International Search Report issued Dec. 23, 2021 in connection with PCT Application No. PCT/EP2021/074921.
Written Opinion of the International Searching Authority issued Dec. 23, 2021 in connection with PCT Application No. PCT/EP2021/074921.

* cited by examiner

*Primary Examiner* — Amy C Bonaparte
(74) *Attorney, Agent, or Firm* — Akerman LLP

(57) ABSTRACT

A process for the production of feed grade urea starting from a liquid urea melt, the process comprising processing the urea melt (6) to promote the formation of biuret until a concentration of at least 3% biuret, and subjecting the so obtained biuret-containing urea melt (8) to a shaping process to obtain a granular urea product.

18 Claims, 1 Drawing Sheet

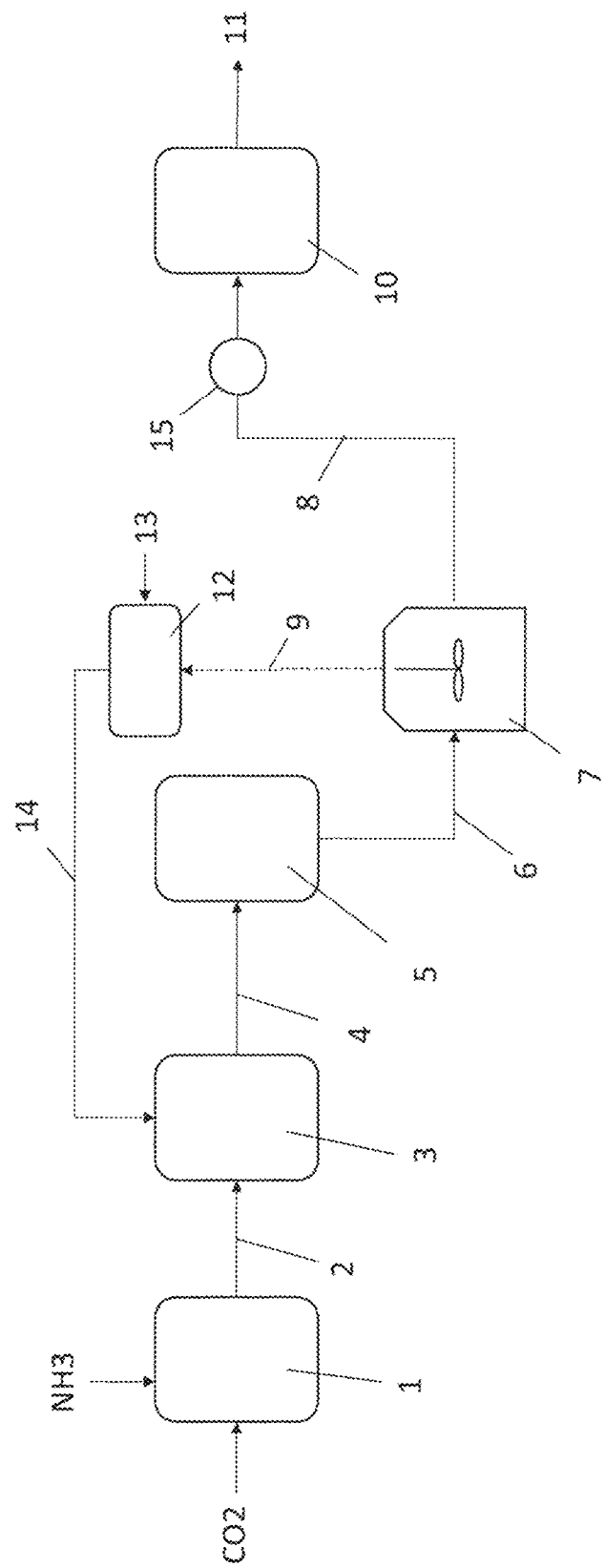

PROCESS FOR PRODUCING FEED-GRADE UREA

CROSS-REFERENCE TO RELATED APPLICATIONS

This application is a national phase of PCT/EP2021/074921, filed Sep. 10, 2021, and claims priority to EP 20206206.3, filed Nov. 6, 2020, the entire contents of both of which are hereby incorporated by reference.

FIELD OF THE INVENTION

The present invention relates to a process for the production of feed grade solid urea.

PRIOR ART

Urea is produced industrially by reacting ammonia and carbon dioxide at suitable urea-forming conditions, typically at a high pressure and high temperature.

Urea is synthesized at a synthesis pressure above 100 bar obtaining a reaction effluent containing urea, water and unconverted reagents mostly in the form of ammonium carbamate. Due to the equilibrium reached in the reaction environment, the amount of unconverted matter in the reaction effluent is significant and the reaction effluent is normally processed for its recover.

In the widely used stripping processes, the reaction effluent is heated in a high-pressure stripper, possibly in the presence of a stripping agent, to decompose the ammonium carbamate and extract gaseous ammonia and carbon dioxide. These are condensed in a high-pressure condenser and recycled to the synthesis reactor. When used, the stripping agent is generally gaseous carbon dioxide or gaseous ammonia.

Said high-pressure stripper and high-pressure condenser may operate at substantially the same pressure as the synthesis reactor, thus forming a high-pressure synthesis section or loop. The urea-containing effluent of the stripper is then processed in one or more recovery sections at a lower pressure to further recover unconverted reagents, obtaining a purified aqueous solution of urea. Said purified solution is essentially made of urea and water and may contain for example about 65% to 70% urea by weight, the balance being water and unavoidable impurities.

Many applications require urea in a solid form. The production of solid urea is also termed finishing or product-shaping.

The most common techniques for urea shaping include prilling and granulation. In both cases, the purified urea solution is treated to remove water, e.g. in a suitable evaporation section. The so obtained liquid urea melt, with a small or negligible content of water, is then converted into solid particles.

In a prilling process the urea melt is distributed in the the form of droplets in a prilling tower where the urea droplets solidify as they fall down in the presence of a counter-current flow of cooling air.

In a granulation process, the urea melt is sprayed on granules, which gradually increase in size as the process continues. A granulation process is often performed in a fluidized-bed condition.

An important aspect of the product shaping techniques is the mechanical properties of the so obtained granular product, particularly the crushing strength. A product with a poor crushing strength is difficult to store and handle because the granules tend to break and form powder. The crushing strength is a relevant factor for the market price of a urea product.

It is known that the mechanical properties of granular urea can be improved by adding formaldehyde to the urea melt before the shaping process. Formaldehyde may be added as such or in the form of a formaldehyde-containing additive such as the additive known as UF80. However the use of formaldehyde as shaping additive introduces concerns of health and environmental sustainability. Formaldehyde is currently classified as a potential cancerous substance.

For the above reasons, the use of formaldehyde as additive in the urea shaping process is not desired or may not be acceptable depending on the application. An example of an application wherein formaldehyde is not desired is the production of feed grade urea. The term feed grade urea denotes urea suitable to be used directly as a feed component for cattle, e.g. ruminants.

SUMMARY OF THE INVENTION

The invention faces the problem of how to produce feed-grade granular urea with acceptable mechanical properties, particularly in terms of crushing strength, but without the use of formaldehyde in the shaping process.

The above problem is solved with a process according to claim 1.

The invention is based on the experimental finding that biuret at a significant concentration improves the mechanical properties of the granular urea product. The applicant has observed that a content of biuret of at least 3% by weight provides a substantial improvement of the crushing strength, comparable to what can be achieved with the conventional addition of formaldehyde.

In the industrial production of urea, biuret is normally regarded as an impurity and efforts are made to avoid its formation. In fertilize-grade urea, for example, the maximum acceptable biuret is normally 1% by weight. In the feed grade urea, on the contrary, a higher content of biuret can be accepted because biuret provides a source of non-protein nitrogen (NPN).

Then the invention is based on the surprising finding that biuret in the feed grade urea is not only acceptable as an alternative source of nitrogen, but also acts like an additive to increase the mechanical strength of the granular urea product.

Accordingly the invention provides that a urea melt is deliberately processed to cause the formation of biuret, before the shaping process. Biuret can be formed by decomposition of urea into biuret and ammonia. Particularly, two moles of urea may decompose into one mole of biuret and one mole of gaseous ammonia. The invention provides that urea melt is processed to promote such decomposition until a target concentration of biuret is reached; then the so obtained biuret-containing urea melt is subjected to a shaping process to obtain the granular product.

PREFERRED EMBODIMENTS

In the preferred embodiments the urea melt is processed until the concentration of biuret is 5% by weight or greater, preferably in a range of 5% to 15%.

The step of processing the urea melt to form biuret may include maintaining the urea melt in a reaction space under biuret-forming conditions for a predetermined residence time until the target concentration of biuret is reached. Said reaction space may be provided by a biuret-forming reactor.

Said biuret-forming conditions includes preferably a temperature in the reaction space of 160° C. to 180° C., preferably 160° C. to 170° C. and more preferably 165° C. or around 165° C. The residence time may be 5 min to 60 min, preferably 20 min.

The urea melt must be maintained above the melting temperature of urea which is around 130° C. As the biuret-forming reaction is performed at a higher temperature, the so obtained biuret-containing urea melt may be cooled to recover heat, provided it remains above the melting temperature. For example a recovery heat exchanger may be installed upstream of the shaping equipment (e.g. granulator or prilling tower).

In a preferred embodiment the reaction space is maintained under a continuously stirred condition during the processing of the urea melt to form biuret. Hence the above mentioned biuret-forming reactor may be a continuously stirred reactor.

The biuret formation process may be a batch process.

The pressure in the reaction space is preferably atmospheric pressure. However the reaction space may be at sub-atmospheric pressure to facilitate the removal of gaseous ammonia and to promote the formation of biuret.

The term urea melt denotes a urea melt obtainable from the evaporation section of a urea plant. In most practical cases it contains at least 96% urea by weight, preferably at least 99%.

The invention allows achieve good mechanical properties of the granular product without the need of additives. In the preferred embodiments of the invention no additive and particularly no formaldehyde is added to the urea melt before the shaping process.

The term of granular product denotes the product obtainable from various shaping processes applicable to the urea field. The preferred shaping processes are granulation and prilling.

The urea melt may be produced in a urea synthesis plant wherein urea is synthesized from ammonia and carbon dioxide at a synthesis pressure obtaining a reaction effluent containing urea, water and unconverted ammonium carbamate; said reaction effluent is processed in one or more recovery sections at a lower pressure to recover unconverted reagents, obtaining a purified aqueous solution of urea; said aqueous solution is processed in an evaporation section to remove water and obtain the urea melt.

Typically the one or more recovery sections include a low-pressure recovery section. Some urea plants, e.g. those using the Snamprogetti self-stripping process, may include additionally a medium-pressure recovery section.

The gaseous ammonia removed from the reaction space where biuret is formed may be recycled to the urea synthesis plant as a source material for the synthesis of urea. For example the ammonia removed from the reaction space may be condensed with water and recycled as ammonia-containing solution. Preferably such solution is recycled to a low-pressure recovery section of the urea plant. Preferably said solution contains at least 15% ammonia by weight.

The invention is susceptible to new plants as well as revamping of existing plants. An existing urea plant may be revamped by adding a biuret-forming reactor between an evaporation section and a shaping section. Accordingly the plant may be adapted to the production of feed-grade urea without formaldehyde.

DESCRIPTION OF THE FIGURE

The FIGURE illustrates a scheme of an implementation of the invention. The following items and process streams are shown.

Item 1 is a synthesis section where ammonia ($NH_3$) and carbon dioxide ($CO_2$) are reacted at high temperature and high pressure to form urea. Said synthesis section 1 may include at least a reactor, a high-pressure stripper and a high-pressure condenser.

Stream 2 is an aqueous solution containing urea, water and unconverted ammonium carbamate. This solution can be withdrawn from the stripper of the synthesis section 1.

Item 3 is a recovery section where the unconverted reagents contained in the solution 2 are recovered and recycled back to the section 1. The unconverted reagents are normally recovered by one or more steps of heating the urea-containing solution for decomposition of ammonium carbamate into gaseous ammonia and CO2, and condensation of said reagents into a carbamate-containing solution which can be pumped back to the reactor or to the condenser of the section 1. The recovery section 3 may operate at one or more pressure levels.

Stream 4 is a purified solution obtained from the recovery section 3. This purified solution 4 contains urea, water and unavoidable impurities.

Item 5 is an evaporation section which removes water from the solution 4.

Stream 6 is a urea melt.

Item 7 is a continuously stirred reactor wherein the urea melt 6 is maintained at suitable biuret-forming conditions so that some urea decomposes into biuret and gaseous ammonia.

Item 8 is a biuret-containing stream withdrawn from the reactor 7.

Item 9 denotes gaseous ammonia removed from the reactor 7.

Item 10 is a urea shaping equipment, for example a granulator or a prilling tower.

Stream 11 is a granular urea product obtained in the urea shaping equipment 10.

Item 12 is a condenser wherein the gaseous ammonia 9 is condensed with the help of water 13.

The stream 14 denotes an aqueous solution of urea obtained in the condenser 12, which is recycled to the recovery section 3.

The item 15 is a heat exchanger where heat can be recovered from the biuret-containing melt, before the shaping process.

It must be noted that the urea solution 4 or the urea melt 6 may be a part of the solution or melt obtained from the recovery section 3 or evaporation 5, respectively. A remaining part of the urea solution or of the urea melt may be directed to a different use or process.

Example: urea melt 6 preferably containing 99.5% urea or more is kept in the reactor 7 for residence time of 20 min, at a temperature of 165° C. and atmospheric pressure. The so obtained melt 8 contains 8% by weight of biuret. This biuret-containing melt after cooling in the heat exchanger 15 is converted into a granular product. The ammonia 9 emerging from the reactor 7 is preferably condensed with water until a solution 14 containing at least 15% ammonia by weight is obtained, said solution 14 can be recycled to the urea plant.

What is claimed is:

1. A process for the production of feed grade urea starting from a liquid urea melt, the process comprising:
    processing the urea melt to form biuret from urea, until a target concentration of biuret in the melt is reached, said target concentration being 3% by weight or higher;
    subjecting the so obtained biuret-containing urea melt to a shaping process to obtain a granular urea product.

2. The process according to claim 1, wherein the target concentration of biuret in the melt is 5% by weight or greater.

3. The process according to claim 1, wherein the step of processing the urea melt to form biuret includes maintaining the urea melt in a reaction space under biuret-forming conditions for a predetermined residence time until said target concentration of biuret is reached.

4. The process according to claim 3, wherein the biuret-forming conditions includes a temperature of 160° C. to 180° C.

5. The process according to claim 3, wherein the residence time is 5 min to 60 min.

6. The process according to claim 3, wherein said reaction space is maintained under a continuously stirred condition during the processing of the urea melt to form biuret.

7. The process according to claim 3, wherein said reaction space is maintained at atmospheric pressure.

8. The process according to claim 1, wherein the urea melt contains at least 96% urea by weight.

9. The process according to claim 1, wherein no formaldehyde is added to the urea melt before the shaping process.

10. The process according to claim 1, wherein the shaping process includes granulation or prilling.

11. The process according to claim 1, further comprising:
reacting ammonia and carbon dioxide at a synthesis pressure in a urea synthesis plant to obtain a reaction effluent containing urea, water and unconverted ammonium carbamate;
processing said reaction effluent in one or more recovery steps at a lower pressure to recover unconverted reagents, obtaining a purified aqueous solution of urea; and
processing said aqueous solution in an evaporation step to remove water and obtain the urea melt.

12. The process according to claim 11, further comprising:
removing gaseous ammonia from a reaction space during the formation of biuret; and
recycling the gaseous ammonia to the urea synthesis plant as a source material for the synthesis of urea.

13. The process according to claim 12, further comprising:
condensing the gaseous ammonia with water; and
recycling said condensed gaseous ammonia and water as aqueous solution of ammonia.

14. The process according to claim 2, wherein the target concentration of biuret in the melt is in a range of 5% to 15% by weight.

15. The process according to claim 3, wherein the biuret-forming conditions includes a temperature of 160° C. to 170° C.

16. The process according to claim 3, wherein the biuret-forming conditions includes a temperature of 165° C.

17. The process according to claim 3, wherein the residence time is 20 min.

18. The process according to claim 1, wherein the urea melt contains at least 99% urea by weight.

* * * * *